United States Patent [19]

Houlsby

[11] Patent Number: 4,521,375
[45] Date of Patent: Jun. 4, 1985

[54] STERILIZING TREATMENT WITH HYDROGEN PEROXIDE AND NEUTRALIZATION OF RESIDUAL AMOUNTS THEREOF

[75] Inventor: Robert D. Houlsby, Sunnyvale, Calif.

[73] Assignee: CooperVision, Inc., Menlo Park, Calif.

[21] Appl. No.: 444,045

[22] Filed: Nov. 23, 1982

[51] Int. Cl.$^3$ .............................................. A61L 2/18
[52] U.S. Cl. ....................................... 422/29; 134/27; 134/28; 206/5.1; 422/30; 422/292
[58] Field of Search ..................... 422/29, 30, 292; 206/5.1; 134/27, 28

[56] References Cited

U.S. PATENT DOCUMENTS

| | | | |
|---|---|---|---|
| 3,025,950 | 3/1962 | Nathan | 206/5.1 |
| 3,621,855 | 11/1971 | Rabinowitz | 206/5.1 |
| 3,912,451 | 10/1975 | Gaglia, Jr. | 422/30 |
| 4,013,410 | 3/1977 | Thomas et al. | 422/30 |
| 4,337,858 | 7/1982 | Thomas et al. | 206/5.1 |
| 4,396,583 | 8/1983 | Le Boeuf | 422/30 X |

OTHER PUBLICATIONS

Brewer et al, Applied and Environmental Microbiology, vol. 34(6), 1977, pp. 797–800.
Flowers et al, Applied and Environmental Microbiology, vol. 33(5), 1977, pp. 1112–1117.
Hurst et al, Canadian Journal of Microbiology, vol. 22, 1976, pp. 677–683.
Martin et al, Applied and Environmental Microbiology, vol. 32(5), 1976, pp. 731–734.
McDonald et al, Applied and Environmental Microbiology, vol. 45(2), 1983, pp. 360–365.
Rayman et al, Canadian Journal of Microbiology, vol. 24, 1978, pp. 883–885.

Primary Examiner—Barry S. Richman
Assistant Examiner—William R. Johnson
Attorney, Agent, or Firm—Vorys, Sater, Seymour and Pease

[57] ABSTRACT

Surfaces and articles or devices sterilized with an aqueous hydrogen peroxide solution are treated with an aqueous solution comprising a sufficient amount of sodium pyruvate to decompose the hydrogen peroxide. The invention includes a method and sterilization system which is particularly useful in medical applications. Hydrophilic contact lenses may be conveniently sterilized with a hydrogen peroxide solution and rendered non-irritating to the eyes by treating the sterilized lenses with a sterile, sodium pyruvate solution which decomposes any hydrogen peroxide remaining with the lenses.

25 Claims, 1 Drawing Figure

STERILIZING TREATMENT WITH HYDROGEN PEROXIDE AND NEUTRALIZATION OF RESIDUAL AMOUNTS THEREOF

BACKGROUND OF THE INVENTION

This invention relates to the use of hydrogen peroxide in disinfection regimens, especially for devices or articles employed in medical applications, and to a means for dissipating residual hydrogen peroxide which may be present on or absorbed in the treated substance or items after disinfection is completed. More particularly, this invention deals with the use of sodium pyruvate to neutralize residual hydrogen peroxide on surfaces or remaining with articles and devices which have been disinfected through contact with dilute aqueous solutions of hydrogen peroxide or hydrogen peroxide producing compositions.

The effectiveness of hydrogen peroxide as a general disinfectant and its use as a germicidal agent in disinfecting a broad range of articles and devices employed in medical applications is well known. Plastic nebulizers, contact lenses, dental appliances, catheters and syringes are but a few of such articles. However, where a residual amount of hydrogen peroxide remains with such articles after treatment, the application of that article to living tissue may cause cellular damage or, at the very least, a significant amount of irritation to the patient. This is particularly true where the disinfected items are particularly or entirely made from materials that may absorb the hydrogen peroxide solution. Soft contact lenses are an important case in point because the very property which allows them to become soft by absorbing up to 150% by weight of water also permits substances which might otherwise be used for cleaning and or sterilization to be absorbed and even concentrated in the lens. When the contact lens is then placed on the eye such substances may be released to irritate and/or harm the sensitive tissues of the conjunctivae or cornea.

In the past when hydrogen peroxide has been utilized in disinfection regimens, various means have been proposed for the neutralization or dissipation of residual hydrogen peroxide. Of course, the simplest but least convenient and perhaps most time consuming method is to simply allow the treated surface to air dry. Another method has been to rinse the treated surfaces with an alkaline solution since hydrogen peroxide is less stable in such an environment. It is also well known that copious rinsing with water or a salt solution will dilute any residual hydrogen peroxide, but as suggested above this approach does not work satisfactorily with plastic components such as a soft contact lens which can absorb the hydrogen peroxide into its matrix. Attempts to dissipate residual hydrogen peroxide from the matrix of such contact lenses have included the incorporation of catalase or peroxidase in the rinsing/storage fluid, but enzymes are proteins which tend to adsorb to the surface being treated, thus diminishing the optical suitability of the lens. A more recent approach to removing residual hydrogen peroxide from contact lenses has been the incorporation of a platinum catalyst in a storage solution after the disinfection step, e.g., see U.S. Pat. No. 3,912,451. Unfortunately, the solid catalyst has a finite useful life and has to be replaced periodically. Furthermore, such catalysts yield undesirable ions into the lens storage solution and these, e.g., ions such as platinum ions, can have an adverse affect on normal corneal physiology.

The present invention represents a significant and unique departure for such concepts and, in a process for sterilizing surfaces and articles or devices with hydrogen peroxide, provides a convenient means for decomposing and removing any residual hydrogen peroxide remaining thereafter with such objects.

SUMMARY OF THE DISCLOSURE

In its broadest aspect this invention comprises the treatment of any bacteria contaminated object or surface with hydrogen peroxide to effect sterilization and thereafter removing any hydrogen peroxide remaining with the treated item by contacting it with a sterile aqueous solution containing pyruvic acid or any water soluble salt thereof, including sodium pyruvate, in an amount which is effective to react with and decompose the hydrogen peroxide. The invention is particularly applicable to any article or device used in medical technology or in the food industry which may be treated with hydrogen peroxide and from which it is important to remove any residual hydrogen peroxide. The invention is specifically important in disinfection regimens for contact lenses and indeed for any article or device used in medical applications which is made in whole or in part from polymeric materials which can adsorb or absorb hydrogen peroxide. In a preferred embodiment the articles to be treated are processed by initially contacting them with a sterilizing aqueous solution of hydrogen peroxide or a solution including a hydrogen peroxide producing compound, and then immersing the sterilized article in a second sterile aqueous solution containing a sufficient amount of sodium pyruvate or any water-soluble salt of pyruvic acid to cause decomposition and neutralization of the residual hydrogen peroxide. More specifically, the concentration of sodium pyruvate required to neutralize hydrogen peroxide is based on a 1:1 molar ratio. Where soft contact lenses are being disinfected, the preferred amount of sodium pyruvate will be determined according to the following formula:

$$\text{mg/ml Sodium Pyruvate} = \frac{A \times B \times C \times 0.323}{D}$$

wherein:
A = wt. of lens in grams
B = percent hydration of lens
C = percent $H_2O_2$
D = volume of disinfecting case in ml
The formula is based on an exact stoichiometric reaction.

DETAILED DESCRIPTION OF THE INVENTION

Figure 1:
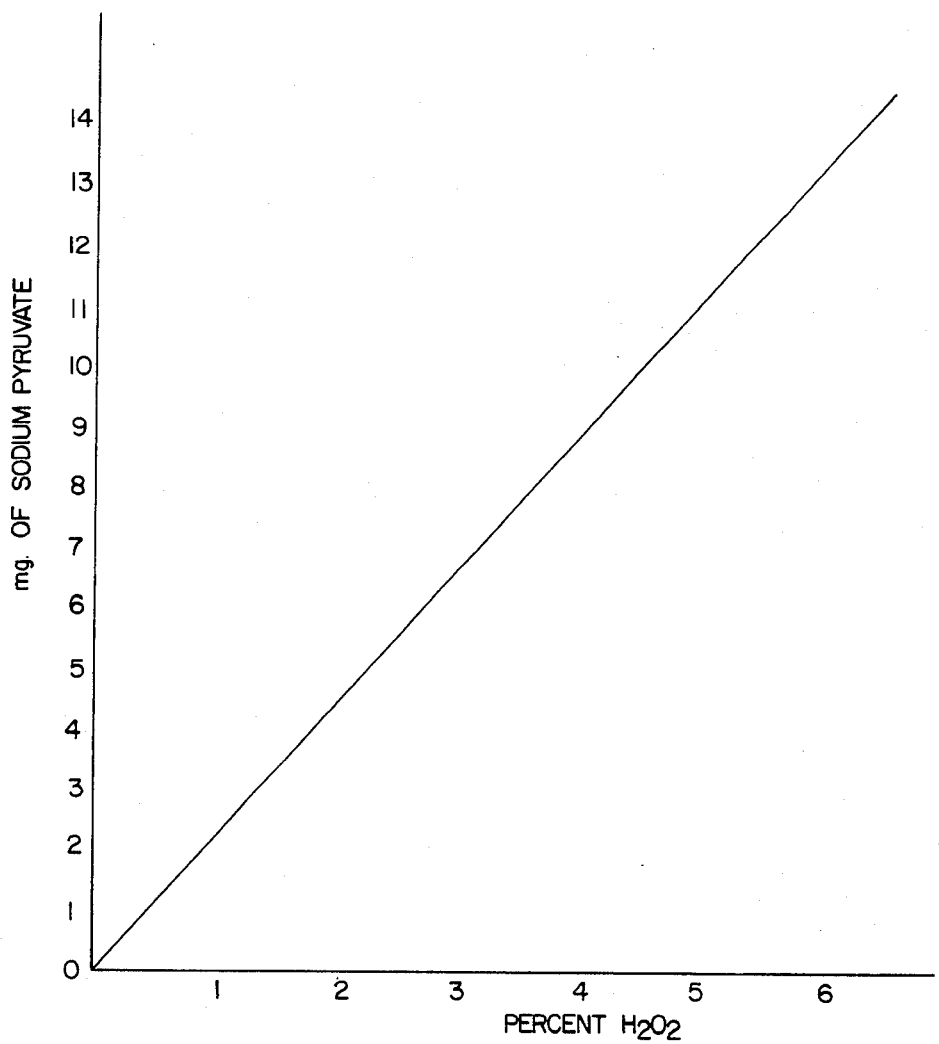

The method of this invention essentially relates to the use of a sufficient amount of a sodium pyruvate solution to effectively neutralize hydrogen peroxide contained in an aqueous sterilizing solution, or to dissipate and remove residual hydrogen peroxide from a surface or from within an object which has been previously treated with such a sterilizing solution. In one embodiment, this method comprises a first step of contacting the object to be sterilized with an aqueous solution containing either hydrogen peroxide itself or a hydrogen peroxide yielding compound. Representative examples of such hydrogen peroxide yielding compounds include metal peroxides, percarbonates, persulphates, perphosphates, peroxyacids, alkylperoxides, acylperoxides, peroxyesters and perborates such as alkali metal perborates. Mixtures of two or more of these substances can also be used in preparing the sterilizing solution. However, in the usual case the solution will contain equivalent hydrogen peroxide, as such, in amounts ranging from about 1 to about 10% by weight, preferably about 1% to 5%, and most preferably about 3% by weight, based on the total volume of the solution. Sterilization of most articles, including contact lenses, is usually accomplished by exposure to the hydrogen peroxide solution for about ten minutes. The terms "sterilizing" or "sterilization" are used in the present invention to mean the rendering non-viable of substantially all pathogenic bacteria of the type typically found including Gram negative and Gram positive bacteria as well as fungi.

The neutralizing solution used in this invention comprises sodium pyruvate, a well known compound which is commercially available from a number of sources. In accordance with the present invention the concentration of sodium pyruvate required to neutralize the hydrogen peroxide used in sterilizing surfaces and articles or devices is based on a 1:1 molar ratio as derived from the following chemical reaction:

$$CH_3COCO_2^- + H_2O_2 \rightarrow CH_3CO_2^- + CO_2 + H_2O.$$

This 1:1 molar ratio allows one to illustrate graphically the concentrations of sodium pyruvate needed to just neutralize $H_2O_2$ concentrations of about 1% to about 6% For example, in FIG. 1 the calculations are based on complete uptake by a pair of Permalens ® lenses, which have been found experimentally to weigh approximately 0.1 gram, and are hydrated to a 70% water content which are assumed to be the worst case for peroxide uptake. The chart gives the mg of sodium pyruvate necessary to neutralize the peroxide taken up by the Permalens ®. To calculate the concentration of sodium pyruvate expressed as mg/ml one divides mg of sodium pyruvate by the volume of the disinfecting case. For example, if one uses 3% $H_2O_2$, then approximately 6.8 mg of pyruvate is needed for neutralization. And if one uses a disinfecting case of total volume of 3 ml, then the concentration needed is 2.3 mg/ml of sodium pyruvate. A general formula when using other lenses is:

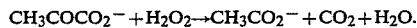

$$\text{mg/ml Sodium Pyruvate} = \frac{A \times B \times C \times 0.323}{D}$$

wherein:
A = wt. of lens in grams
B = percent hydration of lens
C = percent $H_2O_2$
D = volume of disinfecting case in ml.
The formula is based on an exact stoichiometric reaction. The aqueous sodium pyruvate solution may be prepared by a simple mixing of the components at room temperature. A preferred aqueous solution comprises about 0.5% to about 5% by weight sodium pyruvate.

The water used in the sterilizing and neutralizing solutions can be ordinary tap water, but preferably water purified by distillation, filtration, ion-exchange or the like is used. It is especially desirable to use purified water when the article to be cleaned is a hydrophilic gel contact lens or other plastic prosthetic which makes direct contact with living tissue. Also, where hydrophilic contact lenses are being treated it may be important to control the tonicity of the neutralizing solution so that it is compatible, e.g., isotonic, with human serum and tear fluid. That is to say, the solution should be formulated to contain the same salt concentration as that present in the serum and tear fluid of the user. The normal tonicity of human serum and tear fluid is 285-310 milliosmoles/kg. which is equivalent to approximately 9.0 grams of sodium chloride per liter of fluid. Tonicity control and removal of residuals can be achieved by use of isotonic solutions which contain approximately 0.9% sodium chloride, or other salt or mixture of salts having a tonicity approximately equivalent to that of 0.9% sodium chloride. Deviations of plus or minus 20% (i.e., 232-348 milliosmoles/kg.) can be made, but any greater deviation would cause undesirable differences in osmotic pressure between the natural fluids of the eye and the hydrophilic gel lens.

As will be apparent to those of ordinary skill in the art, any soluble salt or mixture of salts compatible with ocular tissue can be used to provide the desired tonicity, although sodium chloride, potassium chloride, or mixtures thereof, are preferred. It is to be understood, however, that one or more essentially neutral water-soluble alkali metal salts can be substituted in whole or in part for the sodium or potassium chloride. Thus, other alkali metal chlorides or alkaline earth metal chlorides such as calcium chloride and magnesium chloride can be used. Other salts such as sodium acetate, sodium sulfate, potassium sulfate, sodium tetraborate, sodium citrate, sodium phosphate, and potassium phosphate may also be useful.

In the usual case, the sodium pyruvate solution will also include a preservative and in most instances any compound which is acceptable for medical applications may be utilized. Where the treated object is for use in the eye, the preservative compound must be ophthalmologically acceptable. Representative examples of such a compound include sorbic acid, edetate salts such as di-, tri-, or tetra-sodium ethylene diamine tetraacetate, benzalkonium chloride, phenylmercuric acetate or nitrate, benzylalcohol, chlorobutanol and sodium thimerosal.

In the preferred method of using this invention with hydrophilic contact lenses, the wearer of such lenses removes them from his eyes and places them in a suitable container with a sufficient amount of a 3% hydrogen peroxide solution to cover the lenses. The lenses are allowed to soak for at least about 5 minutes, preferably 10 minutes, to achieve 99.9 percent kill of bacteria. The lenses are then removed from the container and the sterilizing solution discarded. The lenses are then placed back in the container and immersed in the sodium pyruvate solution for about the same length of time as given in the sterilizing step. The lenses are washed with a sterile aqueous, isotonic, saline solution after which they are ready for wearing.

Other articles within the purview of the invention may be treated in like manner, although it should be emphasized that the neutralizing sodium pyruvate solution may be applied directly to a surface treated with the sterilizing hydrogen peroxide solution or, where an object is immersed therein, to the sterilizing solution itself in the same container.

This invention can be used in connection with the disinfection of a variety of articles and devices such as hard and soft contact lenses, catheters, dressings surrounding indwelling catheters, naso-gastric tubes, endotracheal tubes and surgical instruments. Indeed, this invention may be used in any case where a hydrogen peroxide solution may be employed in disinfection and the removal of residual hydrogen peroxide is important.

The following examples will further illustrate the invention.

EXAMPLE 1

The following is a specific microbiological example of the disinfection of soft contact lenses followed by neutralization with sodium pyruvate. The sodium pyruvate solution has the following composition:

| NEUTRALIZING SOLUTION | |
| --- | --- |
| Poloxamer 407 | 1.0% |
| Sodium Chloride | 0.2% |
| Potassium Chloride | 0.1% |
| Sorbic Acid | 0.2% |
| Sodium Borate | 0.22% |
| Edetate Disodium | 0.1% |
| Boric Acid | 1.0% |
| Sodium Pyruvate | 0.5% |
| Purified Water | Q.S. |

To demonstrate the disinfection procedure, Aquaflex ® soft contact lenses were inoculated with $1.1 \times 10^6$ colony forming units (CFU) of *Pseudomonas aeruginosa* ATCC #9027 suspended in a menstruum of fetal calf serum containing $10^6$ killed yeast cells per ml. This menstruum simulates an organic load consisting of normal tears (the soluble serum portion) and sluffed off skin cells, cosmetics and hair (the particulate yeast cell portion).

The inoculated lenses were cleaned in the palm of the hand for 20 seconds with Pliagel ®, a surfactant cleaner commercially available from Cooper Laboratories, Inc. The Pliagel ® was rinsed from the lenses using one bottle of Unisol ®, unit dose saline, 15 ml, commercially available from Cooper Laboratories, Inc.

Eight lenses were subdivided into four sets of two each following the above treatment. Two lenses were soaked in 3% $H_2O_2$ for 10 minutes then cultured in nutrient broth for five days at 32°–34° C.; neither lens exhibited growth indicating disinfection. Two other lenses were soaked in the neutralizing solution for 10 minutes then cultured; one lens exhibited growth, indicating lack of disinfection. Two lenses were soaked in 3% $H_2O_2$ for 10 minutes followed by soaking for 0.5 minutes in the neutralizing solution then cultured; neither exhibited growth indicating the disinfecting "regimen" was effective. Two additional lenses were soaked for 10 minutes in premixed 3% $H_2O_2$ and the neutralizing solution combined in a ratio of 1:13 then cultured; one lens exhibited growth, indicating the neutralization of $H_2O_2$ by the neutralizing solution. Two incubated, untreated lenses exhibited growth when cultured (positive controls) and two uninoculated, untreated lenses did not exhibit growth when cultured (negative controls).

EXAMPLE 2

The following is an example of the disinfection of gauze wound dressings followed by neutralization with sodium pyruvate solution. The pyruvate solution has the same composition as given in the previous example.

To demonstrate the disinfection procedure, eight pieces of sterile gauze, two inch square, were inoculated with $1.1 \times 10^6$ CFU of *Pseudomonas aeruginosa* ATCC #9027 suspended in organic load. Two pieces of gauze were soaked in 3% $H_2O_2$ for 10 minutes then cultured in nutrient broth for five days at 32'–34° C.; neither one exhibited growth, indicating disinfection. Two other pieces of gauze were soaked in the neutralizing solution for 10 minutes then cultured; both pieces exhibited growth, indicating lack of disinfection. Two pieces of gauze were soaked in 3% $H_2O_2$ for 10 minutes followed by soaking for 0.5 minutes in the neutralizing solution, then cultured; neither one exhibited growth, indicating the disinfecting "regimen" was effective. Two additional pieces of gauze were soaked for 10 minutes in premixed 3% $H_2O_2$ and the neutralizing solution combined in a ratio of 1:13, then cultured; both pieces of gauze exhibited growth, indicating the neutralization of $H_2O_2$ by the neutralizing solution, thereby preventing disinfection. Two inoculated untreated pieces of gauze exhibited growth when cultured (positive controls) and two uninoculated, untreated pieces of gauze did not exhibit growth when cultured (negative controls).

It is readily apparent from this example that any and all types of wound dressings can be disinfected and neutralized to become biocompatible with injured tissues by using the $H_2O_2$-pyruvate system. These dressings include those used around indwelling catheters and the disinfection procedure can be done in some instances without removing the dressing.

EXAMPLE 3

The following is an example of the disinfection of catheters followed by neutralization with sodium pyruvate solution. The pyruvate solution has the same composition as given in the previous example.

To demonstrate the disinfection procedure, eight catheters were inoculated with $1.1 \times 10^6$ CFU *Pseudomonas aeruginosa* ATCC #9027 suspended in organic load. The catheters consisted of six-inch sections of Tygon tubing (1/32 ID, 3/32 OD, 1/32 Wall) each connected to 21 gauge, 1½ inch long needle. The inoculum was aspirated into the catheter by connecting the needle to a one cc syringe. Two of the inoculated catheters were immersed in and flushed with 3% $H_2O_2$ for 10 minutes then cultured in nutrient broth for five days at 32°–34° C.; neither catheter exhibited growth, indicating disinfection. The other two catheters were soaked in the neutralizing solution for 10 minutes then cultured; both catheters exhibited growth, indicating lack of disinfection. Two catheters were soaked for 10 minutes in $H_2O_2$ followed by soaking for 0.5 minutes in the neutralizing solution, then cultured; neither one exhibited growth, indicating the disinfecting "regimen" was effective. Two additional catheters were soaked for 10 minutes in premixed 3% $H_2O_2$ and the neutralizing solution combined in a ratio of 1:13, and cultured. Both catheters exhibited growth, indicating the neutralization of $H_2O_2$ by the neutralizing solution, thereby preventing disinfection. Two inoculated, untreated catheters exhibited growth when cultured (positive controls) and two uninoculated, untreated catheters did not exhibit growth when cultured (negative controls).

It follows from this example that any and all catheters compatible with 3% $H_2O_2$ and sodium pyruvate can be disinfected and neutralized by this system to become biocompatible with mucus membranes. This system can be especially useful during surgery where, for example, a catheter, e.g., Swan-Genz, is contaminated during manipulation and must be disinfected before reuse. This disinfection-neutralization system may also be useful in emergency rooms during similar situations.

Furthermore, it follows from this example that medical tubing, such as naso-gastric tubes, can be disinfected and neutralized either in place or for reuse. In addition, the blade portion of an endotracheal tube can be disinfected and neutralized for reuse in emergency room situations.

Since the outside and fluid path of catheters and tubes can be disinfected and neutralized by this system, one can extend its use to medical instruments in general, especially during in-use situations. These situations may arise in operating or emergency rooms where surgical instruments need to be reused.

Other situations that may require reuse of medical instruments include those occurring in dental offices. That is to say, dental devices such as dentures, bite plates and braces may be disinfected and neutralized by this system. Use of this system may, also be extended to other medical devices such as vaporizers and nebulizers.

EXAMPLE 4

The following is an example of the time required to neutralize $H_2O_2$ with sodium pyruvate. Approximately equal molar ratios of the two ingredients were allowed to react for five minutes.

The volume of 3% $H_2O_2$ (equivalent to 0.88 molar) used in the reaction was one ml. The volume of 1.1% sodium pyruvate (equivalent to 0.1 molar) used in the reaction was 10 ml. The composition of the sodium pyruvate solution was as follows:

| | |
|---|---|
| Sorbic Acid | 0.1% |
| Sodium Pyruvate | 1.1% |
| Disodium Edetate | 0.1% |
| Sodium Chloride | 0.6% |
| Potassium Chloride | 0.2% |
| Sodium Borate | 0.22% |
| Poloxamer 407 | 1.0% |
| Thimerosal | 0.001% |
| Purified Water | Q.S. |

The amount of residual peroxide remaining in solution after the reaction time was found to be less than 500 ppm as determined by the potassium dichromate ($K_2Cr_2O_7$) test, as referenced in Gasset, A. R. et al., "Hydrogen Peroxide Sterilization of Hydrophilic Contact Lenses," Arch.Ophthalmol. 93: 412–415, June 1975. Therefore, the neutralization time of 3% $H_2O_2$ by 1.1% sodium pyruvate mixed together in a 1:10 v/v ratio appears to be less than five minutes.

EXAMPLE 5

The following example demonstrates the safety of the sodium pyruvate solution to ocular tissue. The composition of the neutralizing solution is given in Example 1.

The irritating potential of the neutralizing solution compared to saline was evaluated in rabbit eyes. The neutralizing solution was instilled hourly for an eight hour period into the right eyes of six rabbits. Saline was instilled simultaneously into the left eyes of the six rabbits. Each eye of each rabbit was examined periodically throughout the 72-hours of observation both macroscopically and with the slit lamp.

No evidence of conjunctival, iridal, or corneal irritation was seen in any eye at any time throughout this study. This acute, multiple-exposure, ocular safety study demonstrates that the neutralizing solution is non-irritating to rabbit ocular tissue.

EXAMPLE 6

This example demonstrates the safety of the disinfection-neutralization system for use with soft contact lenses. The sodium pyruvate solution has the same composition as given in Example 1.

Three groups of six rabbits each wore a Permalens ® soft contact lens in the right eye for a one hour wearing period. Group I wore lenses which had been soaked in 3% $H_2O_2$, Group II wore lenses which had been soaked in the neutralizing solution, and Group III wore lenses which had been soaked in 3% $H_2O_2$ and then soaked in the neutralizing solution. All lenses were soaked in each test material for ten minutes. After lens removal, both eyes were examined macroscopically and with the slit lamp periodically during the 72-hour observation period.

Macroscopic examinations of lens wearing eyes in Group I revealed mild to moderate conjunctival irritation, iris irritation, and mild to moderate corneal opacity in all rabbits. These signs of ocular irritation persisted throughout the study with no significant change except in the case of conjunctival irritation. At hour 24, conjunctival chemosis and discharge had subsided but moderate to severe redness was noted. However, by hour 72, no chemosis or discharge was seen and redness had subsided to mild or moderate.

Slit lamp examinations of lens wearing eyes in Group I revealed moderate dilation of the vessels of the conjunctiva, nictitating membrane and scleral/limbal tissue. In addition, all rabbits had moderate corneal opacity with staining and moderate injection of iridal vessels. These signs persisted throughout the study with no significant change with the exception of the nictitating membrane. By hour 72, all rabbits exhibited only mild nictitating membrane irritation.

Macroscopic and slit lamp examinations of lens wearing eyes in Group II and III showed no signs of ocular irritation throughout the study.

Macroscopic and slit lamp examinations of non-lens wearing eyes in all groups revealed no remarkable signs of irritation at any time during the study.

It readily follows from this example that any and all types of contact lenses (soft, hard or gas permeable lenses) can be safely used in the eye when exposed to this disinfection-neutralization system.

While the invention has been described principally with respect to aqueous solutions of hydrogen peroxide and pyruvic acid salts, especially sodium pyruvate, it should be clear that this invention encompasses the use of such pyruvate compounds or hydrogen peroxide yielding compounds in solid form. For example, a kit may comprise a container including an appropriate amount of solvent, preferably purified water, a sufficient amount of a solid, hydrogen peroxide yielding compound such that when dissolved in the solvent it provides an effective sterilizing solution, and a sufficient amount of pyruvate to decompose and neutralize any residual hydrogen peroxide which exists after sterilization of the treated object.

Accordingly, it should be understood that this invention may be embodied in other specific forms without departing from its spirit or essential characteristics. The embodiments described above are to be considered in all respects as illustrative and not restrictive, the scope of the invention being indicated by the appended claims rather than by the foregoing description, and all changes which come within the meaning and range of equivalency of the claims are intended to be embraced therein.

I claim:

1. A method for sterilizing surfaces which come into contact with living tissue comprising
   (a) contacting said surface with an aqueous medium containing a sterilizing amount of hydrogen peroxide, and
   (b) subsequently contacting said surface with an amount of pyruvic acid or a water-soluble salt thereof effective to destroy any residual hydrogen peroxide.

2. The method of claim 1 wherein said aqueous medium of step (a) contains from about 1% to about 5% by weight of hydrogen peroxide, based on the total volume of the solution.

3. The method of claim 2 wherein said aqueous medium of step (a) is a 3% by weight solution of hydrogen peroxide.

4. The method of claim 2 wherein said surface is first immersed in said aqueous medium of step (a), then removed from said medium and immersed in the solution of step (b).

5. The method of claim 1 wherein said pyruvic acid or said thereof is contained in a sterile aqueous solution.

6. The method of claim 5 wherein said water-soluble salt of pyruvic acid is sodium pyruvate.

7. The method of claim 5 wherein said pyruvic acid or said thereof is contained in a sterile, isotonic, buffered, aqueous solution.

8. The method of claim 5 wherein said sterile aqueous solution of sodium pyruvate comprises about 0.5 to about 5% by weight of sodium pyruvate.

9. The method of claim 8 wherein said aqueous medium of step (a) is a 3% by weight solution of hydrogen peroxide and said sterile aqueous solution of step (b) contains about 5 to about 50 milligrams of sodium pyruvate per milliliter.

10. A method of sterilizing a contact lens without imparting ocular irritating after-effects to the lens, comprising
    (a) contacting said lens with an aqueous medium containing a sterilizing amount of hydrogen peroxide, and
    (b) subsequently contacting said lens with an amount of pyruvic acid or a water-soluble salt thereof effective to destroy any residual hydrogen peroxide.

11. The method of claim 10 wherein said pyruvic acid or said thereof is contained in a sterile aqueous solution.

12. The method of claim 11 wherein said water-soluble salt of pyruvic acid is sodium pyruvate.

13. The method of claim 12 wherein said sterile aqueous solution of sodium pyruvate comprises about 0.5 to about 5% by weight of sodium pyruvate.

14. The method of claim 11 wherein said lens is a hydrophilic contact lens.

15. The method of claim 14 wherein said sterile aqueous solution also comprises ophthalmologically acceptable amounts of tonicity adjusting agents and buffering compounds.

16. The method of claim 14 wherein said sterilizing is conducted within a disinfecting case and the amount of said sodium pyruvate is determined according to the following formula:

$$\text{mg/ml sodium pyruvate} = \frac{A \times B \times C \times 0.323}{D}$$

wherein:
A = weight of lens in grams
B = percent hydration of lens
C = percent $H_2O_2$
D = volume of disinfecting case in ml.

17. A sterilization system for decontaminating articles and devices which come into contact with living tissue comprising
    (a) an aqueous hydrogen peroxide sterilizing solution, and
    (b) a neutralizing, sterile, aqueous solution comprising from about 0.5 to about 5% by weight of pyruvic acid or a water-soluble salt thereof effective to neutralize the hydrogen peroxide contained in said sterilizing solution.

18. A contact lens sterilization system according to claim 17 wherein the sterilizing solution is a 3% by weight hydrogen peroxide solution and the neutralizing solution contains an amount of sodium pyruvate according to the following formula $$\text{mg/ml sodium pyruvate} = \frac{A \times B \times C \times 0.323}{D}$$

wherein:
A = weight of lens in grams
B = percent hydration of lens
C = percent $H_2O_2$
D = volume of disinfecting case in ml.

19. A sterilization kit for articles which come into contact with living tissue comprising
    (a) a container containing a sufficient amount of a hydrogen peroxide-yielding compound effective, when dissolved in a selected volume of water whereby a sterilizing solution is produced, to sterilize a treated article, and
    (b) a container containing a sufficient amount of a water-soluble pyruvic acid salt effective to prepare an aqueous solution containing from about 5 to about 50 mg/ml of said salt, and
    (c) means for holding said containers substantially immobile in said kit.

20. The kit of claim 19 wherein said hydrogen peroxide-yielding compound is selected from the group consisting of peroxides, percarbonates, persulfates, perphosphates, peroxyacids, alkylperoxides, acylperoxides, peroxyesters and perborates.

21. The kit of claim 19 wherein said pyruvic acid salt is sodium pyruvate.

22. A sterilization kit for articles which come into contact with living tissue comprising
    (a) a container containing an aqueous sterilizing solution containing an amount of hydrogen peroxide effective to sterilize said article, and
    (b) a container containing an amount of a water-soluble salt of pyruvic acid effective to prepare an aqueous solution containing from about 5 to about 50 mg/ml of said salt, and
    (c) means for holding said containers substantially immobile in said kit.

23. The kit of claim 22 wherein said sterilizing solution contains about 3% by weight hydrogen peroxide and the pyruvic acid salt is sodium pyruvate.

24. The kit of claim 22 wherein said sodium pyruvate is dissolved in a sterile, aqueous solution.

25. The kit of claim 24 wherein said sterile aqueous solution also comprises ophthalmologically acceptable amounts of tonicity adjusting agents and buffering compounds.

* * * * *